US010969323B2

(12) United States Patent
Al Readean et al.

(10) Patent No.: US 10,969,323 B2
(45) Date of Patent: Apr. 6, 2021

(54) SYSTEMS AND METHODS FOR SPECIAL CORE ANALYSIS SAMPLE SELECTION AND ASSESSMENT

(71) Applicant: Saudi Arabian Oil Company, Dhahran (SA)

(72) Inventors: Muhammad S. Al Readean, Dammam (SA); Abdullah A. Alakeely, Tarout (SA); Endurance O. Ighodalo, Rakkah (SA)

(73) Assignee: Saudi Arabian Oil Company, Dhahran (SA)

( * ) Notice: Subject to any disclaimer, the term of this patent is extended or adjusted under 35 U.S.C. 154(b) by 342 days.

(21) Appl. No.: 15/992,871

(22) Filed: May 30, 2018

(65) Prior Publication Data

US 2019/0368994 A1    Dec. 5, 2019

(51) Int. Cl.
*G01N 15/08* (2006.01)
*G01N 33/24* (2006.01)

(52) U.S. Cl.
CPC ............. *G01N 15/08* (2013.01); *G01N 33/24* (2013.01)

(58) Field of Classification Search
CPC ................................ G01N 15/08; G01N 33/24
See application file for complete search history.

(56) References Cited

U.S. PATENT DOCUMENTS

| 9,097,821 B2 | 8/2015 | Skalinski et al. |
| 2013/0262028 A1 | 10/2013 | De Prisco et al. |
| 2014/0297186 A1 | 10/2014 | Suarez-Rivera et al. |
| 2015/0355353 A1 | 12/2015 | Whitaker et al. |
| 2016/0076369 A1 | 3/2016 | Ziauddin et al. |
| 2016/0231450 A1 | 8/2016 | Shao et al. |
| 2016/0305237 A1 | 10/2016 | Klemin et al. |
| 2017/0017011 A1* | 1/2017 | Howard ............... G01N 15/088 |
| 2017/0018096 A1 | 1/2017 | Sungkorn et al. |

(Continued)

OTHER PUBLICATIONS

Corbett et al., "Petrotype-based Sampling Applied in a Saturation Exponent Screening Study, Nubian Sandstone Formation, Sirt Basin, Libya", Petrophysics, 51(4), 2010, pp. 264-270.*

(Continued)

*Primary Examiner* — Catherine T. Rastovski
(74) *Attorney, Agent, or Firm* — Bracewell LLP; Constance G. Rhebergen; Christopher L. Drymalla

(57) ABSTRACT

Provided are embodiments of conducting a special core analysis (SCAL) of an identified subset of core samples. Embodiments include determining rock quality values for core samples extracted from a subsurface hydrocarbon formation, and determining static rock types corresponding to the core samples based on the rock quality values. For each of the static rock types identified, scaling the corresponding rock quality values to generate scaled rock quality values, and determining a number of subspaces ($n_s$) for the static rock type based on the scaled rock quality values. For each subspace of the static rock type: identifying a number (k) of most similar rock quality values in the subspace; identifying a subset of the core samples corresponding to the most similar rock quality values identified for the subspace of the static rock type; and conducting a SCAL of the core samples of the subset of the core samples.

16 Claims, 9 Drawing Sheets

(56) References Cited

U.S. PATENT DOCUMENTS

2017/0123098 A1  5/2017  Wang et al.

OTHER PUBLICATIONS

Siddiqui et al., "Improvements in the Selection Criteria for Representative Special-Core-Analysis Samples", SPE Reservoir Evaluation & Engineering, Dec. 2006.*

AAPG Wiki; "Rock quality" available as of Feb. 15, 2018 at: http://wiki.aapg.org/Rock_quality#What_is_r35.3F; pp. 1-5.

Doyle, J.K. et al.; "Mean Distance in a Graph" Discrete Mathematics 17 (1977); pp. 147-154.

Fitch, Peter J.R. et al.; "An integrated and quantitative approach to petrophysical heterogeneity" Marine and Petroleum Geology 63 (2015); pp. 82-96.

Kolodzie JR., Stanley; "Analysis of Pore Throat Size and Use of the Waxman-Smits Equation to Determine OOIP in Spindle Field, Colorado" SPE 9382, 55th Annual Fall Technical Conference & Exhibition of the Society of Petroleum Engineers, Sep. 21-24, 1980; pp. 1-10.

Rebelle, Michel et al.; "Rock-typing in Carbonates: A Critical Review of Clustering Methods" SPE-171759-MS, Abu Dhabi International Petroleum Exhibition & Conference, Nov. 10-13, 2014; pp. 1-14.

Corbett et al., "Petrotype-based Sampling Applied in a Saturation Exponent Screening Study, Nubian Sandstone Formation, Sirt Basin, Libya", Petrophysics, 2010, pp. 264-270, vol. 51, No. 4, Society of Petrophysics and Well Log Ananysis.

International Search Report and Written Opinion for related PCT application PCT/US2019/034673 dated Sep. 23, 2019.

Mohammed et al., "How many Relative Permeability Measurements do you need ? A case Sudy from a North African reservoir", Petrophysics, 2003, pp. 262-270, vol. 44, No. 4, Society of Petrophysics and Well Log Analysis.

Siddiqui et al., "Improvements in the Selection Criteria for Representative Special-Core-Analysis Samples", SPE Reservoir Evaluation & Engineering, 2006, pp. 647-653, Society of Petroleum Engineers.

* cited by examiner

SYSTEMS AND METHODS FOR SPECIAL CORE ANALYSIS SAMPLE SELECTION AND ASSESSMENT

FIELD

Embodiments relate generally to assessment of core samples, and more particularly to special core analysis sample selection and assessment.

BACKGROUND

Petroleum exploration and production typically emphasizes optimizing hydrocarbon production, such as oil or gas, from a hydrocarbon reservoir. This can include employing certain drilling, completion and production operations at a well, or a field of wells, to maximize hydrocarbon production from the reservoir. In the context of drilling operations, this can include drilling a well at location and trajectory to facilitate the extraction of hydrocarbons from the reservoir. In the context of completion operations, this can include configuring a well to facilitate the extract hydrocarbons from a wellbore of the well. In the context of production operations, this can include operating wells in a manner to facilitate the extraction of hydrocarbons from the reservoir. This can include employing enhanced oil recovery (EOR) techniques, such as thermal injection, gas injection and chemical injection, to assist in extracting hydrocarbons from the reservoir. These and other techniques for optimizing hydrocarbon production typical rely on accurate assessments of reservoir properties, such as formation rock porosity, permeability and wettability, to determine a formation's potential for hydrocarbon production, and suitable techniques for optimizing hydrocarbon production from a reservoir in the formation.

In many instances, rock samples of a geologic formation, often referred to as "core samples", are extracted and assessed to determine properties of the geologic formation. For example, during drilling of a well into a formation (e.g., a subsurface formation known to contain or at least suspected to contain hydrocarbons), a coring operation can be conducted to extract a core sample from the formation. The core sample may be transported to a laboratory, where it is subjected to core analysis, to determine properties of the core sample and, in turn, properties of the formation at or near the location from which the core sample was extracted. This information can be used, for example, to calibrate log and seismic measurements, to determine well placements, well trajectories, well completion designs, well production strategies or other parameters for optimizing hydrocarbon production from wells.

In some instances, core samples are subjected to special core analysis ("SCAL" or "SPCAN"). SCAL involves a relatively extensive analysis in comparison to routine or conventional core analysis. SCAL normally includes extensive assessments, such measurements of two-phase flow properties, and determining relative permeability and capillary pressure, that are not conducted in routine or conventional core analysis. The information obtained by way of SCAL can provide an increased level of information with regard to properties of the core sample and the formation and, thus, can be useful in optimizing hydrocarbon production from wells.

SUMMARY

Applicants have recognized that extensive core sample assessments, such as special core analysis ("SCAL" or "SPCAN"), can be expensive and time consuming and, as a result, may not be economically feasible for all core samples. For example, although conducting a SCAL of all or a large number of the core samples extracted from one or more wells drilled into a formation may provide an extensive amount of information regarding properties of the formation, a well operator may not have the financial budget or the time to conduct a SCAL of all or a large number of the core samples. As a result, a well operator may resort to forgoing SCAL or selecting a limited number of the core samples for SCAL. In such a scenario, a well operator may attempt to select core samples that are most representative of the formation, for SCAL analysis. Unfortunately, selecting core samples that are most representative of the formation is not a straightforward task. As a result, a well operator may not select appropriate core samples for SCAL, in turn, wasting time and money. For example, a well operator may fail to select an breadth of cores samples that provides a suitable representation of the formation, resulting in undersampling that does not provide a complete and accurate representation of the formation; or a well operator may select and analyze more samples than are needed to obtain a complete and accurate representation of the formation, resulting in oversampling that unnecessarily increases time and costs for developing the formation.

Recognizing these and other shortcomings of existing techniques for core sample assessment, Applicants have developed novel systems and methods for selection and assessment of core samples. Such techniques may reduce the potential for oversampling and undersampling, helping to avoid petrophysical misrepresentations of formations and to avoid unnecessary costs. The described embodiments can provide an objective assessment of core samples based on a less intensive preliminary core analysis, to identify appropriate core samples to be subjected to a more intensive SCAL. This can reduce the time and costs associated with assessing core samples and, in turn, help to optimize hydrocarbon production from a reservoir in a cost efficient manner.

In some embodiments, relatively basic core sample data, such as permeability and porosity, are determined by way of a preliminary core analysis, rock quality values are determined for each of the core samples based on the core sample data, static rock types of the core samples are determined based on the rock quality values, sampling subspaces are determined for each of the static rock types, and representative core samples are selected from the sampling subspaces. The representative core samples may, then, be subject to SCAL to generate SCAL data that provides additional information regarding properties of the core samples and the formation. The SCAL data can, in turn, be used to optimize hydrocarbon production from the formation in a cost efficient manner. For example, the SCAL data may be used to calibrate log and seismic measurements, or to determine well placements, well trajectories, well completion designs, well production strategies or other parameters for optimizing hydrocarbon production from wells.

In some embodiments, the sampling subspaces for the static rock types are determined based on objective driven constraints. In a "minimum coverage" scenario (e.g., intended to provide a minimum number of samples for sampling the minimum, maximum and medium distributions within a static rock type), the distribution of the static rock type may be divided into three equal subspaces (e.g., first, second and third subspaces defined by a $0\text{-}33^{rd}$ percentile, a $33^{rd}\text{-}66^{th}$ percentile and a $66^{th}\text{-}100^{th}$ percentile of rock quality values corresponding to the static rock type. In a "classification-constrained" scenario, the distribution of the static rock type may be divided into a given number of subspaces, equal to a number of different classes identified in the static rock type (e.g., zonal, geological or facies-based classes identified in the static rock type). In an "optimal coverage" scenario (e.g., intended to optimize a coverage to cost ratio), the distribution of the static rock type may be divided into a given number of subspaces based on heterogeneity within the static rock type, in an effort to increase sampling of heterogeneous static rock types or reduce sampling of homogeneous static rock types.

In some embodiments, relevant percentiles within the subspaces are identified, and core samples corresponding to the percentiles within the subspaces are selected for SCAL. Such a methodical and objective preliminary assessment of core samples to select core samples to be subjected to SCAL can provide consistent and repeatable core sample selections and assessments. This can reduce the time and costs associated with assessing core samples, and, in turn, help to optimize hydrocarbon production from a reservoir in a cost efficient manner.

Provided in some embodiments is a method that includes the following: obtaining core sample data for core samples extracted from a subsurface hydrocarbon formation, the core sample data including rock properties for each core sample of the core samples, the rock properties for each core sample including a porosity of the core sample, and a permeability of the core sample; determining, for each core sample of the core samples and based on the core sample data, a rock quality value for the core sample, and the rock quality value for the core sample defined by the porosity of the core sample and the permeability of the core sample; determining, based on the rock quality values for the core samples, static rock types corresponding to the core samples, each of the static rock types corresponding to a subset of the core samples having a rock quality value corresponding to the static rock type; for each of the static rock types identified: scaling the rock quality values corresponding to the static rock type to generate scaled rock quality values corresponding to the static rock type, each scaled rock quality value including a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1; determining, based on the scaled rock quality values, a number of subspaces ($n_s$) for the static rock type; and for each subspace of the static rock type: identifying, using mathematical optimization, a number (k) of most similar rock quality values in the subspace; identifying a subset of the core samples corresponding to the most similar rock quality values identified for the subspace of the static rock type; and conducting a special core analysis (SCAL) of each of the core samples of the subset of the core samples corresponding to the most similar rock quality values identified for the subspace of the static rock type.

In some embodiments, determining the static rock types corresponding to the core samples includes segmenting a distribution of the rock quality values using expectation-maximization mixture modeling clustering to determine the static rock types corresponding to the core samples. In some embodiments, the expectation-maximization mixture modeling clustering includes a flow zone indicator method or a Winland $R_{35}$ method. In certain embodiments, segmenting a distribution of the rock quality values using expectation-maximization mixture modeling clustering to determine the static rock types corresponding to the core samples includes defining curves corresponding to expectation-maximization mixture modeling clustering, and determining a static rock type for each region bounded by at least one of the curves and containing at least one rock quality value of the distribution of the rock quality values.

In some embodiments, scaling the rock quality values corresponding to the static rock type to generate scaled rock quality values corresponding to the static rock type includes: determining a permeability range for the static rock type, the permeability range for the static rock type defined by a maximum permeability and a minimum permeability of the subset of the core samples corresponding to the static rock type; determining a porosity range for the static rock type, the porosity range for the static rock type defined by a maximum porosity and a minimum porosity of the subset of the core samples corresponding to the static rock type; scaling, based on the permeability range, the permeability ($K_i$) of each of the rock quality values corresponding to the static rock type according to the following relationship:

$$SK_i = \frac{K_i - \text{Min}(K)}{\text{Max}(K) - \text{Min}(K)},$$

where Max(K) is the maximum permeability of the subset of the core samples corresponding to the static rock type, and Min(K) is the minimum permeability of the subset of the core samples corresponding to the static rock type; and scaling, based on the porosity range, the porosity ($\Phi_i$) of each of the rock quality values corresponding to the static rock type according to the following relationship:

$$S\Phi_i = \frac{\Phi_i - \text{Min}(\Phi)}{\text{Max}(\Phi) - \text{Min}(\Phi)},$$

where Max($\Phi$) is the maximum porosity of the subset of the core samples corresponding to the static rock type, and Min($\Phi$) is the minimum porosity of the subset of the core samples corresponding to the static rock type.

In certain embodiments, determining a number of subspaces ($n_s$) for the static rock type includes employing a minimum coverage scenario including determining the number of subspaces ($n_s$) for the static rock type to be equal to three, and identifying three subspaces for the static rock type including a first subspace defined by a $0$-$33^{rd}$ percentile of the scaled rock quality values corresponding to the static rock type, a second subspace defined by a $33^{rd}$-$66^{th}$ percentile of the scaled rock quality values corresponding to the static rock type, and a third subspace defined by a $66^{th}$-$100^{th}$ percentile of the scaled rock quality values corresponding to the static rock type. In some embodiments, determining a number of subspaces ($n_s$) for the static rock type includes employing a classification constrained scenario including determining a number of different classes identified in the static rock type ($n_c$), and determining the number of subspaces ($n_s$) for the static rock type to be equal to the number of different classes identified in the static rock type ($n_c$). In certain embodiments, determining a number of subspaces ($n_s$) for the static rock type includes employing an optimal coverage scenario including: determining a heterogeneity coefficient for the static rock type, the heterogeneity coefficient for the static rock type defining a degree of heterogeneity of the subset of the core samples corresponding to the static rock type; and determining the number of subspaces ($n_s$) for the static rock type based on heterogeneity within the static rock type. In some embodiments, determining the number of subspaces ($n_s$) for the static rock type based on heterogeneity within the static rock type includes determining the number of subspaces ($n_s$) for the static rock type to be equal to a number of subspaces ($S_i$) that maximizes the following objective function:

$$\sum_i^n VDP_{N_i} * S_i,$$

where, $$\sum_i^n S_i \leq \frac{K}{k},$$

where $$M \leq S_i \leq \frac{K}{k} VDP_{N_i},$$

where M is a minimum threshold $S_i$ is an integer, $i \in \{1, 2, \ldots, n\}$ is an index for each of the respective static rock types determined, n is a number of static rock types determined, K is a total number of core samples to be selected from the static rock types determined, k is the number of core samples to select for each subspace of the static rock type, and $VDP_{N_i}$ is a normalized heterogeneity coefficient for the static rock type of index i. In certain embodiments, the heterogeneity coefficient for the static rock type includes a normalized Dykstra-Parsons coefficient ($V_{dp}$) determined for the static rock type.

In some embodiments, identifying the number (k) of most similar scaled rock quality values in the subspace includes: determining a sample percentile (Px) defining a percentile in the subspace to sample from; determining a percentile point ($\Phi_p, K_p$) defined by a percentile porosity ($\Phi_p$) corresponding to the sample percentile (Px) and a percentile permeability ($K_p$) corresponding to the sample percentile (Px); and determining, from the rock quality values in the subspace, the number (k) of closest scaled rock quality values in the subspace, defined by the number (k) of rock quality values of the rock quality values in the subspace, determined to be closest to the percentile point ($\Phi_p, K_p$).

In some embodiments, the sample percentile ($Px_s$) for a subspace and the closest rock quality values in the subspace are determined based on the following objective function:

$$\mu(\Gamma) = \frac{\sum_{u,w \in V(\Gamma)}^n d(u, w)}{\binom{k}{2}},$$

where Px is an integer, $Px_s - Px_{(s-1)} \leq$ percentile boundaries of the subspace, d(u, w) is a Euclidean distance between two points u and w, $V(\Gamma)$ is a vertex set of k points corresponding to the most similar points to select given $k=|V(\Gamma)|$ and S is number of subspaces in the static rock type. In certain embodiments, identifying the subset of the core samples corresponding to the most similar rock quality values identified for the subspace of the static rock type includes generating a listing of selected core samples including the subset of the core samples corresponding to the most similar rock quality values identified for the subspace of the static rock type.

In some embodiments, conducting a SCAL of each of the core samples of the subset of the core samples corresponding to the most similar rock quality values identified for the subspace of the static rock type includes generating SCAL core analysis data including measurements of two-phase flow properties, relative permeability or capillary pressure for the core samples of the subset of the core samples corresponding to the most similar rock quality values identified for the subspace of the static rock type. In certain embodiments, conducting a SCAL of each of the core samples of the subset of the core samples corresponding to the most similar rock quality values identified for the subspace of the static rock type includes generating SCAL core analysis data, and the method further including, based on the SCAL core analysis data, calibrating log or seismic measurements, or determining well placements, well trajectories, well completion designs, well production strategies for optimizing hydrocarbon production from wells. In certain embodiments, the method further includes conducting coring operations to extract the core samples from the subsurface hydrocarbon formation.

Provided in some embodiments is a non-transitory computer readable storage medium having program instructions stored thereon that are executable by a processor to perform the following operations: obtaining core sample data for core samples extracted from a subsurface hydrocarbon formation, the core sample data including rock properties for each core sample of the core samples, the rock properties for each core sample including a porosity of the core sample, and a permeability of the core sample; determining, for each core sample of the core samples and based on the core sample data, a rock quality value for the core sample, the rock quality value for the core sample defined by the porosity of the core sample and the permeability of the core sample; determining, based on the rock quality values for the core samples, static rock types corresponding to the core samples, each of the static rock types corresponding to a subset of the core samples having a rock quality value corresponding to the static rock type; for each of the static rock types identified: scaling the rock quality values corresponding to the static rock type to generate scaled rock quality values corresponding to the static rock type, each scaled rock quality value including a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1; determining, based on the scaled rock quality values, a number of subspaces ($n_s$) for the static rock type; and for each subspace of the static rock type: identifying, using mathematical optimization, a number (k) of most similar rock quality values in the subspace; identifying a subset of the core samples corresponding to the most similar rock quality values identified for the subspace of the static rock type; and conducting a special core analysis (SCAL) of each of the core samples of the subset of the core samples corresponding to the most similar rock quality values identified for the subspace of the static rock type.

Provided in some embodiments is a system that includes a special core analysis (SCAL) system, and a core samples selection system. The core samples selection system being adapted to perform the following operations: obtaining core sample data for core samples extracted from a subsurface hydrocarbon formation, the core sample data including rock properties for each core sample of the core samples, the rock properties for each core sample including a porosity of the core sample, and a permeability of the core sample; determining, for each core sample of the core samples and based on the core sample data, a rock quality value for the core sample, the rock quality value for the core sample defined by the porosity of the core sample and the permeability of the core sample; determining, based on the rock quality values for the core samples, static rock types corresponding to the core samples, each of the static rock types corresponding to a subset of the core samples having a rock quality value corresponding to the static rock type; and for each of the static rock types identified: scaling the rock quality values corresponding to the static rock type to generate scaled rock quality values corresponding to the static rock type, each scaled rock quality value including a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1; determining, based on the scaled rock quality values, a number of subspaces ($n_s$) for the static rock type; for each subspace of the static rock type: identifying, using mathematical optimization, a number (k) of most similar rock quality values in the subspace; and identifying a subset of the core samples corresponding to the most similar rock quality values identified for the subspace of the static rock type. The SCAL system being adapted to conduct a special core analysis (SCAL) of each of the core samples of the subset of the core samples corresponding to the most similar scaled rock quality values identified for the subspace of the static rock type.

Figure 1:
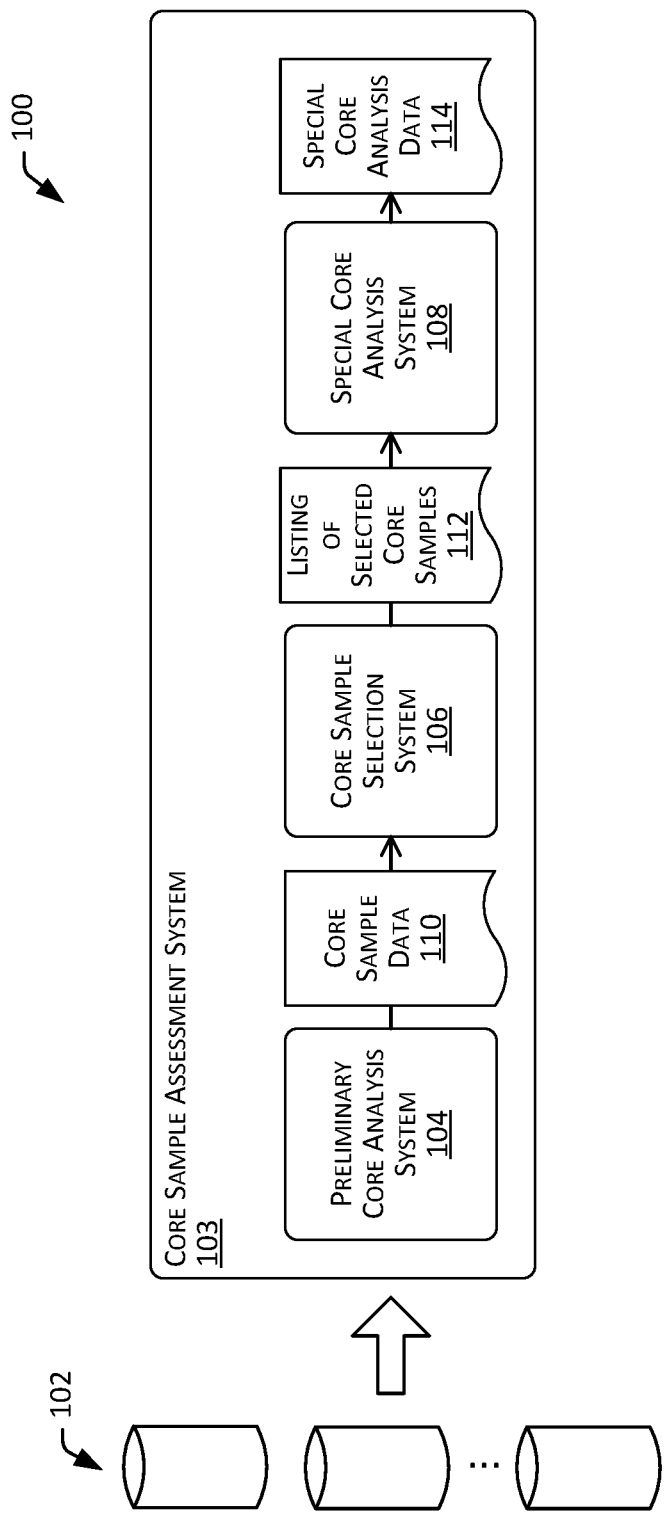
FIG. 1 is diagram that illustrates a core sample assessment environment in accordance with one or more embodiments.

While this disclosure is susceptible to various modifications and alternative forms, specific embodiments are shown by way of example in the drawings and will be described in detail. The drawings may not be to scale. It should be understood that the drawings and the detailed descriptions are not intended to limit the disclosure to the particular form disclosed, but are intended to disclose modifications, equivalents, and alternatives falling within the spirit and scope of the present disclosure as defined by the claims.

DETAILED DESCRIPTION

Described are embodiments of novel systems and methods for selection and assessment of core samples. Such techniques may reduce the potential for oversampling and undersampling, helping to avoid petrophysical misrepresentations of formations and to avoid unnecessary costs. The described embodiments can provide an objective assessment of core samples based on a less intensive preliminary core analysis, to identify appropriate core samples to be subjected to a more intensive special core analysis ("SCAL" or "SPCAN"). This can reduce the time and costs associated with assessing core samples and, in turn, help to optimize hydrocarbon production from a reservoir in a cost efficient manner.

In some embodiments, relatively basic core sample data, such as permeability and porosity, are determined by way of a preliminary core analysis, rock quality values are determined for each of the core samples based on the core sample data, static rock types of the core samples are determined based on the rock quality values, sampling subspaces are determined for each of the static rock types, and representative core samples are selected from the sampling subspaces. The representative core samples may, then, be subject to SCAL to generate SCAL data that provides additional information regarding properties of the core samples and the formation. The SCAL data can, in turn, be used to optimize hydrocarbon production from the formation a cost efficient manner. For example, the SCAL data may be used to calibrate log and seismic measurements, or to determine well placements, well trajectories, well completion designs, well production strategies or other parameters for optimizing hydrocarbon production from wells.

In some embodiments, the sampling subspaces for the static rock types are determined based on objective driven constraints. In a "minimum coverage" scenario (e.g., intended to provide a minimum number of samples for sampling the minimum, maximum and medium distributions within a static rock type), the distribution of the static rock type may be divided into three equal subspaces (e.g., first, second and third subspaces defined by a $0$-$33^{rd}$ percentile, a $33^{rd}$-$66^{th}$ percentile and a $66^{th}$-$100^{th}$ percentile of rock quality values corresponding to the static rock type. In a "classification-constrained" scenario, the distribution of the static rock type may be divided into a given number of subspaces, equal to a number of different classes identified in the static rock type (e.g., zonal, geological or facies-based classes identified in the static rock type). In an "optimal coverage" scenario (e.g., intended to optimize a coverage to cost ratio), the distribution of the static rock type may be divided into a given number of subspaces based on heterogeneity within the static rock type, in an effort to increase sampling of heterogeneous static rock types or reduce sampling of homogeneous static rock types.

In some embodiments, relevant percentiles within the subspaces are identified, and core samples corresponding to the percentiles within the subspaces are selected for SCAL. Such a methodical and objective preliminary assessment of core samples to select core samples to be subjected to SCAL can provide consistent and repeatable core sample selections and assessments. This can reduce the time and costs associated with assessing core samples, and, in turn, help to optimize hydrocarbon production from a reservoir in a cost efficient manner.

FIG. 1 is a diagram that illustrates a core sample assessment environment 100 in accordance with one or more embodiments. In the illustrated embodiment, the core sample assessment environment 100 includes core samples 102 and a core sample assessment system ("CSAS") 103.

The core samples 102 may include rock samples of a geologic formation. The formation may be a subsurface hydrocarbon formation known to contain, or at least suspected to contain, deposits of hydrocarbons, such as a hydrocarbon reservoir. In some embodiments, the core samples 102 are extracted from a formation by way of a well drilled into the formation. For example, during drilling of a hydrocarbon production well, an injection well or a monitoring well, into a formation, a well operator may drill to a depth corresponding to a location (or "zone of interest") (e.g., using a conventional drill bit), and conduct a coring operation (e.g., using a coring bit), to extract (e.g., to the surface) a core sample 102 (e.g., a cylindrically shaped sample of the formation rock) from the location. The core sample 102 may be representative of formation rock in and around the locations. Such a coring operation can be conducted at various locations with the wellbore of the well, or at various locations within wellbores of wells drilled into the formation, to obtain core samples 102 representative of different locations within the formation. The core samples 102 may be provided to laboratory (e.g., including the core sample assessment system 103) for assessment of their respective rock properties.

In some embodiments, the core sample assessment system 103 includes a systems for analyzing the core samples 102. In the illustrated embodiment, the core sample assessment system 103 includes a preliminary core analysis system 104, a core sample selection system 106 and special core analysis (SCAL) system 108. In some embodiments, the core sample assessment system 103 may control aspects of coring operations undertaken to obtain core samples 102. In some embodiments, the core sample assessment system 103 includes a computer system that is the same or similar to that of computer system 1000 described with regard to FIG. 8.

The preliminary core analysis system ("PCA system") 104 may include a system for conducting an initial analysis of the core samples 102, such as a routine core analysis of the core samples 102, to generate corresponding core sample data 110 for the core samples 102. In some embodiments, the core sample data 110 for the core samples 102 includes relatively basic core sample data, such as a location (e.g., a depth or three dimensional coordinate) from which the core sample was extracted from the formation, permeability, porosity, fluid saturation, grain density, lithology and texture, for each of the core samples 102 determined by way of the initial core analysis. In some embodiments, the PCA system 104 includes a module of the core sample assessment system 103, or a computer system that is the same or similar to that of computer system 1000 described with regard to FIG. 8.

The core sample selection system ("CSS system") 106 may include a system for conducting an assessment of the core sample data 110 to generate a listing of selected core samples 112. In some embodiments, the listing of selected core samples 112 for the core samples 102, includes a listing of a subset of the core samples 102 that are selected for further analysis, such as SCAL. As described, in some embodiments, the CSS system 106 determines rock quality values for each of the core samples 102 based on the core sample data 110, determines static rock types of the core samples 102 based on the rock quality values, determines sampling subspaces for each of the static rock types, selects a representative subset of the core samples 102 from the sampling subspaces, and populates the listing of selected core samples 112 with the representative subset of the core samples 102. In some embodiments, the CSS system 106 includes a module of the core sample assessment system 103, or a computer system that is the same or similar to that of computer system 1000 described with regard to FIG. 8.

Generally there are different types of test performed in SCAL. The tests include porosity, permeability and grain density measurements (stressed and without stressed conditions), electrical properties measurement (formation factor and resistivity index), rock wettability, relative permeability, Nuclear Magnetic Resonsnce (NMR) measurements and Mercury Injection Capillary Pressure (MICP) measurement. Others SCAL tests include X-ray diffraction analysis, lithology descriptions and scanning electron microscopy. The special core analysis system ("SCAL system") 108 may include a system for conducting an extensive analysis of the selected subset of the core samples 102, to generate SCAL data 114 for the selected subset of the core samples 102. The SCAL system 108 may include a SCAL test fixture for physically subjecting core samples 102 to various experiments to determine properties of the core samples 102. In some embodiments, the SCAL data 114 for the core samples 102, includes relatively extensive data for the core samples 102 that is not provided by way of the initial analysis of the core samples 102, such as measurements of two-phase flow properties, relative permeability and capillary pressure for the core samples 102. The SCAL data 114 can provide an increased level of information with regard to properties of the core samples 102 and the portions of the formation they were extracted from. This information can be useful in optimizing hydrocarbon production from wells. For example, the SCAL data 114 may be used to calibrate log and seismic measurements for the formation, to determine well placements for a field of wells in the formation, well trajectories for wells in the formation, well completion designs for wells in the formation, well production strategies for wells in the formation, or other parameters for optimizing hydrocarbon production from wells in the formation. The results of SCAL analysis are sometimes used to calibrate log data (LWD or Wireline) and seismic data. Porosity and permeability measurement are sometimes used to calibrate log analysis porosity and permeability. Formation factor (FF) and resistivity index (RI) generate cementation factor (M) and saturation exponent (N) are sometimes used as input in water saturation calculation. X-ray diffraction measurements are sometimes used to calibrate mineralogy interpretation from logs. Rock wettability can be important for optimizing oil recovery, as it can influence reservoir performance, particularly in water flooding and enhanced oil recovery techniques. Relative permeability is the ratio of effective permeability of a particular fluid at a particular saturation to absolute permeability of that fluid at total saturation. Relative permeability can be used in the comparison of the different abilities of fluids to flow in the presence of each other, since the presence of more than one fluid generally inhibits flow. NMR measurements can be used to determine total porosity as well as porosity partitioning (e.g., clay and capillary bound and free fluids). NMR measurements can sometimes be used to estimate permeability and saturation above free water level. NMR SCAL measurements can sometimes be used to establish parameters for NMR logging. MICP data can sometimes be used for rock typing and defining saturation height function. Lithology descriptions can sometimes be integrated in the definition of rock types. In some embodiments, the SCAL system 108 includes a module of the core sample assessment system 103, or a computer system that is the same or similar to that of computer system 1000 described with regard to FIG. 8.

Figure 2:
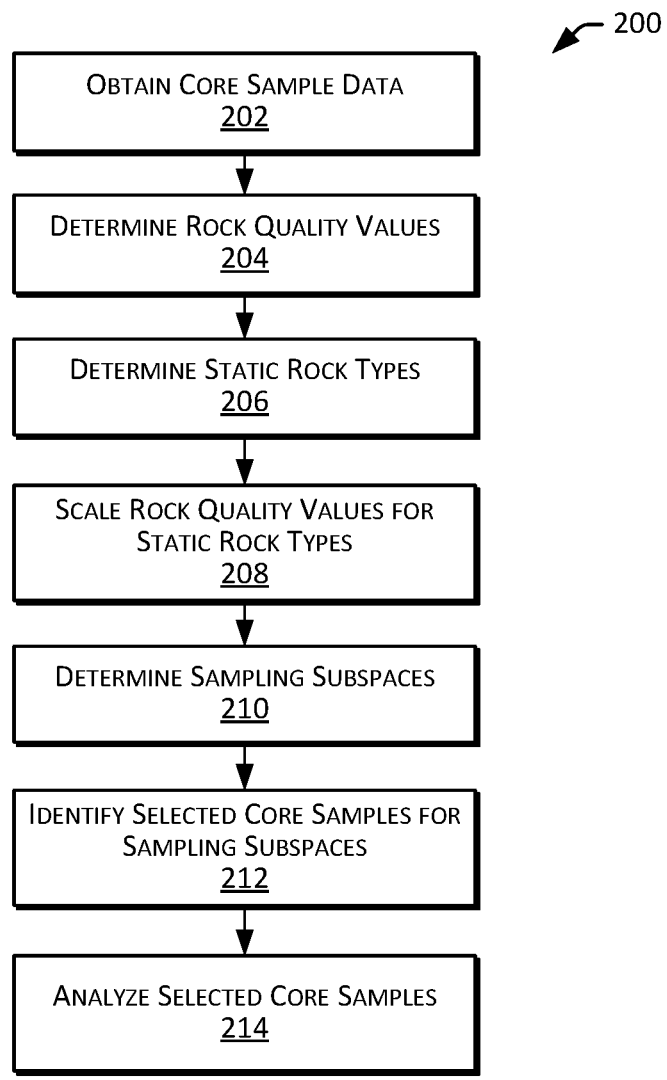
FIG. 2 is a flowchart that illustrates a method of core sample selection and assessment in accordance with one or more embodiments.

FIG. 2 is a flowchart that illustrates a method 200 of core sample selection and assessment in accordance with one or more embodiments. In some embodiments, method 200 includes obtaining core sample data (block 202), determining rock quality values (block 204), determining static rock types (block 206), scaling the rock quality values for the static rock types (block 208), determining sampling subspaces (block 210), identifying selected core samples for the sampling subspaces (block 212), and analyzing the selected core samples (block 214). In some embodiments, some or all of the operations of method 200 are performed by the core sample assessment system 103.

In some embodiments, obtaining core sample data (block 202) includes generating core sample data based on a preliminary core analysis of core samples. For example, obtaining core sample data may include the PCA system 104 conducting an initial analysis of the core samples 102, such as a routine core analysis of the core samples 102, to generate core sample data 110 for the core samples 102. In some embodiments, the core sample data 110 for the core samples 102 includes relatively basic core sample data, such as permeability, porosity, fluid saturation, grain density, lithology and texture, for each of the core samples 102 determined by way of the initial core analysis.

In some embodiments, determining rock quality values (block 204) includes determining rock quality values for each of the core samples. For example, determining rock quality values may include the CSS system 106 determining rock quality values for each of the core samples 102. In some embodiment, the rock quality value for a given core sample 102 is be defined by a permeability value and a porosity value for the core sample 102, provided in the core sample data 110. For example, if the core sample data 110 specifies a permeability ($K_1$) and a porosity ($\Phi_1$) for a first core sample ($CS_1$), a rock quality value for the first core sample ($CS_1$) may be defined as ($\Phi_1$, $K_1$). Rock quality values may be determined in a similar manner for each of core samples 102, to generate rock quality values (e.g., ($\Phi_1$, $K_1$), ($\Phi_2$, $K_2$), ..., ($\Phi_n$, $K_n$)) for each of the core samples 102 (e.g., $CS_1$, $CS_2$, ..., $CS_n$). Although rock quality values defined by permeability and porosity are described for the purpose of illustration, embodiments can include other rock quality measures, such as grain density.

Figure 3:
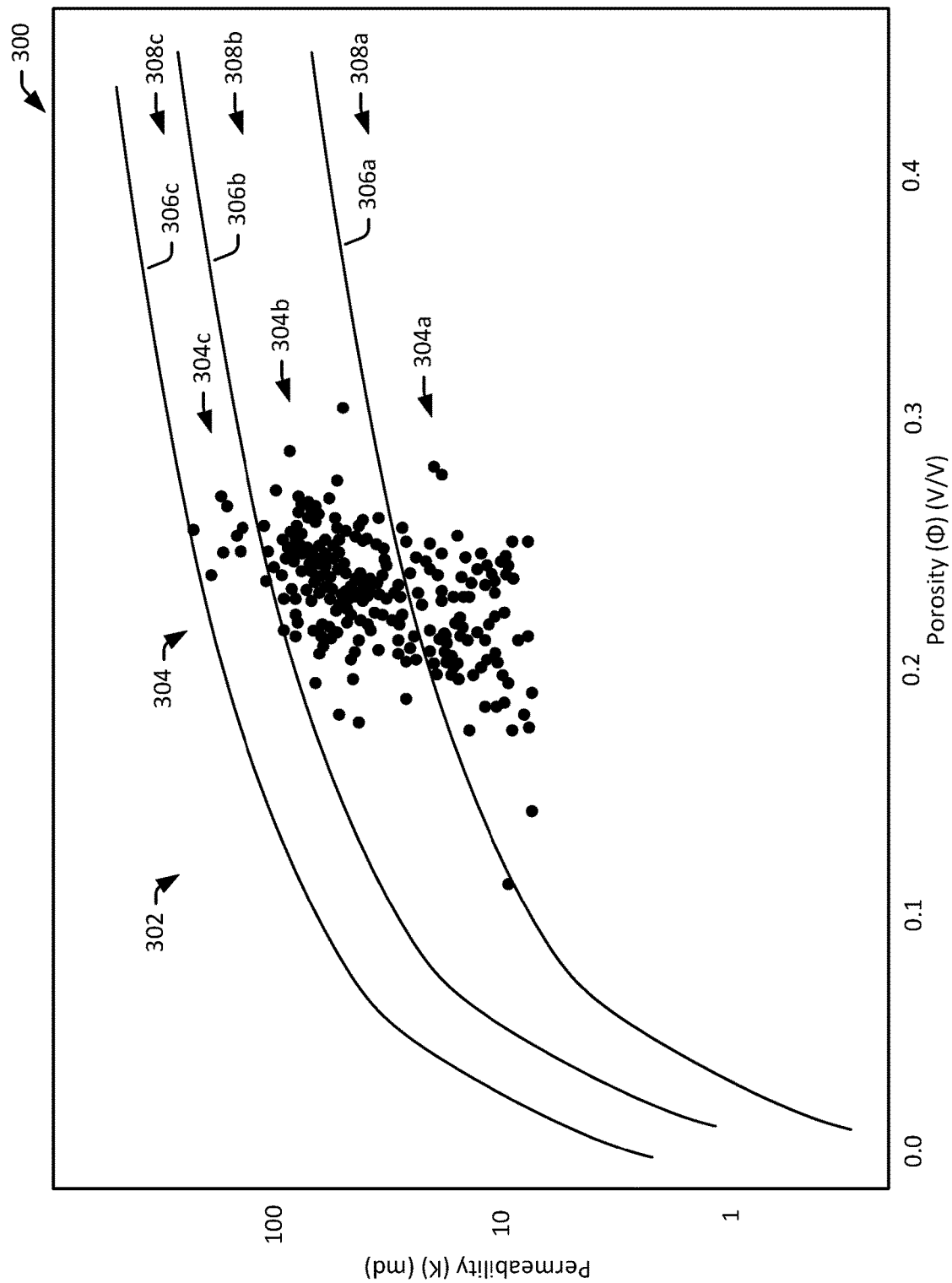
FIG. 3 is a chart that illustrates an example distribution of rock quality values and corresponding static rock types in accordance with one or more embodiments.

In some embodiments, determining static rock types (block 206) includes determining static rock types corresponding to the rock quality values for the core samples. For example, determining static rock types can include the CSS system 106 determining static rock types corresponding to a distribution of the rock quality values (e.g., ($\Phi_1$, $K_1$), ($\Phi_2$, $K_2$), ..., ($\Phi_n$, $K_n$)) for the core samples (e.g., $CS_1$), ($CS_1$), ..., $CS_n$). In some embodiments, this includes grouping (or "clustering") the rock quality values into similar pore types or over-all rock qualities. The grouping can include, generating a histogram of the distribution of the rock quality values and segmenting the distribution into different groups (or "clusters") of rock quality values. The segmenting may be conducted by way of expectation-maximization mixture modeling, such as clustering based on groupings defined by the flow zone indicator (or "log(FZI)") method or the Winland $R_{35}$ (or "$R_{35}$") method. Details regarding the FZI method are described in Rebelle M. and Lalanne B., 2014, Rock-Typing In Carbonates: A Critical Review Of Clustering Methods, SPE-171759-MS, which is incoproated by reference. Details regarding the Winland $R_{35}$ method are described by Kolodzie, S. J., 1980, The analysis of Pore throat Size and Use of Waxman-Smit to Determind OOIP in Spindle Field, Colo.: SPE 55$^{th}$ Annual Fall Tech. Conf. and Exhib., SPE paper 0382), which is incoproated by reference. The expectation-maximization mixture modeling can be used to generate curves to define static rock type groups within the distribution of permeability vs. porosity of the rock quality values (e.g., FZI and Winland $R_{35}$ rock quality values). FIG. 3 is a chart that illustrates an example distribution 300 of rock quality values 302 in accordance with one or more embodiments. In the illustrated embodiment, the distribution of rock quality values 302 includes rock quality value points 304, with each rock quality value point being defined by a respective rock quality value ($\Phi_i$, $K_i$) for a core sample 102. These example rock quality value points 304 have porosity values ($\Phi_i$, $\Phi_2$, ..., $\Phi_n$) in a range of about 0.1 V/V (pore volume/total volume) to about 0.3 V/V, and have permeability values ($K_1$, $K_2$, ..., $K_n$) in a range of about 8 milliDarcy (md) to about 200 md. Further, the illustrated embodiment includes three rock typing curves 306a, 306b and 306c, defining three regions 308a, 308b and 308c containing rock quality value points 304. The first (lower) region 308a has an upper bound defined by the first rock typing curve 306a, and contains a first subset (or "cluster") of the rock quality value points 304a. The second (middle) region 308b has a lower bound defined by the first rock typing curve 306a, and an upper bound defined by the second rock typing curve 306b, and contains a second subset of the rock quality value points 304b. The third (upper) region 308c has a lower bound defined by the second rock typing curve 306b, and an upper bound defined by the third rock typing curve 306c, and contains a third subset of the rock quality value points 304c. Each of the three rock typing curves 306a, 306b and 306c may be defined, for example, by way of a given expectation-maximization mixture modeling clustering method, such as that defined by the log(FZI) method or the $R_{35}$ method. For example, the three rock typing curves 306a, 306b and 306c may be defined by $R_{35}$ values of 2.408, 5.357 and 8.454, respectively, using the $R_{35}$ method. The values defining the curves to define static rock type groups within a distribution of permeability vs. porosity of the rock quality values may be selected by a well operator (e.g., a petrophyscist), or otherwise predefined. The rock typing curves 306a, 306b and 306c may define groupings of rock quality value points 304 representing similar pore types or over-all rock quality. Each of these grouping may define a particular rock type. That is the first, the second and the third regions 308a, 308b and 308c may correspond to first, second and third rock types, respectively, and the first, the second and the third subsets (or "clusters") of rock quality value points 304a, 304b and 304c may be grouped (or "clustered") into the first, the second and the third rock types, respectively. The core samples 102 may, in turn, be grouped into rock types based on the grouping of their respective rock quality value. For example, the core samples 102 corresponding to the first, the second or the third subsets of rock quality value points 304a, 304b and 304c may be grouped into the first, the second and the third static rock types, respectively. As a result, the first, the second and the third static rock types may be determined for the set of rock quality values 304.

In some embodiments, scaling rock quality values for static rock types (block 208) includes, for each static rock type determined, scaling the permeability and porosity values of the cluster of rock quality values corresponding to the static rock type. Continuing with the prior example, scaling rock quality values for static rock types can include the CSS system 106, for each of the three static rock types determined, scaling the permeability and porosity values of the rock quality values corresponding to the rock type. This may include, for each of the first, the second and the third clusters of rock quality value points 304a, 304b and 304c, scaling the corresponding permeability and porosity values. In some embodiments, scaling rock quality values for a given static rock type includes determining a permeability range defined by a maximum permeability and a minimum permeability of the cluster of rock quality values corresponding to the static rock type (e.g., a maximum permeability and a minimum permeability of the subset of the core samples 102 corresponding to the static rock type), determining a porosity range defined by a maximum porosity and a minimum porosity of the cluster of rock quality values of corresponding to the static rock type (e.g., a maximum porosity and a minimum porosity of the subset of the core samples 102 corresponding to the static rock type), and scaling, based on the permeability range and the porosity range, the cluster of rock quality values corresponding to the static rock type, to generate a cluster of scaled rock quality values for the static rock type. Each scaled rock quality value may be defined by a corresponding scaled permeability value and a corresponding scaled porosity value. The scaling may provide that the scaled permeability values of the scaled rock quality values corresponding to the static rock type are scaled to span a range of 0 to 1, and that the scaled porosity values of the scaled rock quality values corresponding to the static rock type are scaled to span a range of 0 to 1. Such scaling may reduce influences of different units and disproportionate value differences between permeability and porosity, which may otherwise be biased by porosity values. For example, the permeability may range between 0.1 to 5000 md while porosity values may range between 0 and 0.45 V/V, and, thus, subsequent calculations based on unscaled values may be porosity biased. In some embodiments, a scaled value $SV_i$ (e.g., a scaled porosity or permeability value) for a given unscaled value ($v_i$) (e.g., an un-scaled porosity or permeability value) is conducted in accordance with the following relationship:

$$SV_i = \frac{v_i - \text{Min}(v)}{\text{Max}(v) - \text{Min}(v)}, \quad (1)$$

where Max(v) is the maximum value in the range of the parameter (e.g., a maximum porosity or maximum permeability), and Min(v) is the minimum value in the range of the parameter (e.g., a minimum porosity or minimum permeability).

Figure 4:
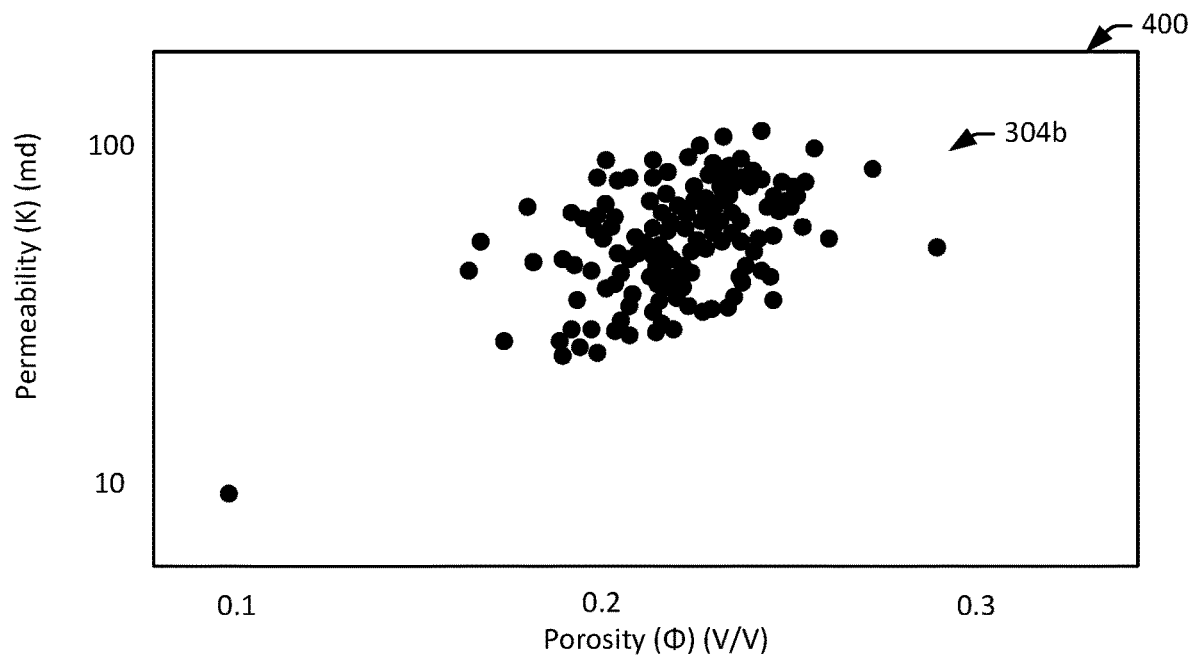
FIGS. 4 and 5 are charts that illustrate distributions of un-scaled rock quality values and distributions of corresponding scaled rock quality values, respectively, for a given static rock type in accordance with one or more embodiments.
Figure 5:
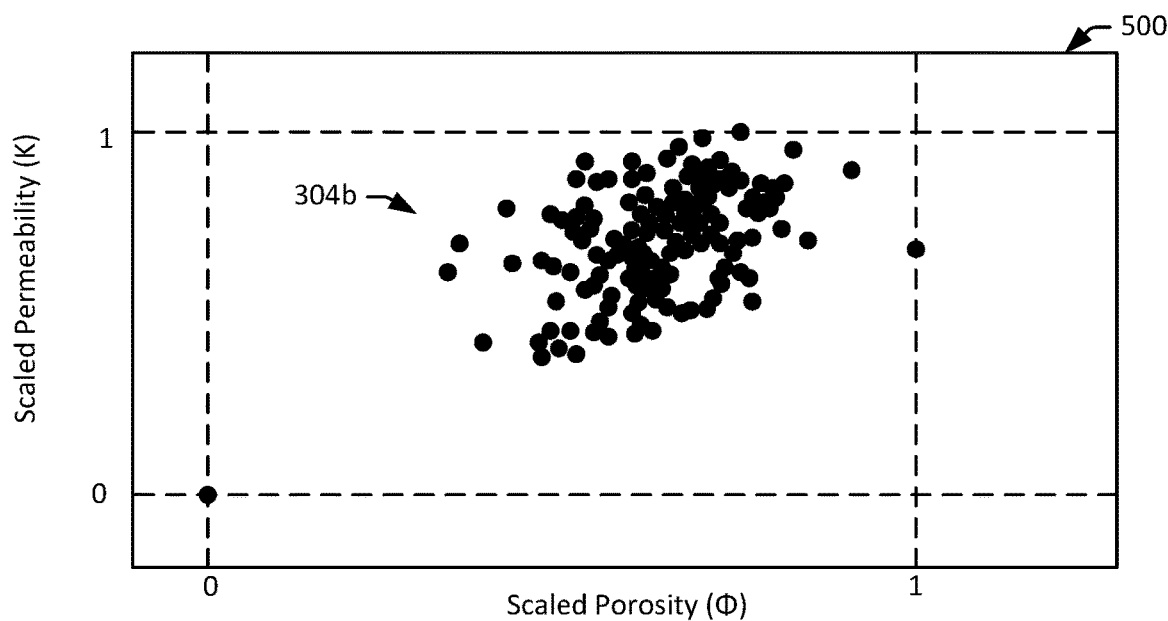

FIG. 4 is chart that illustrates an example unscaled distribution 400 of the second cluster of rock quality value points 304b of FIG. 3, in accordance with one or more embodiments. FIG. 5 is chart that illustrates an example scaled distribution 500 of the second cluster of rock quality value points 304b of FIG. 3, in accordance with one or more embodiments. As can be seen, the unscaled distribution 400 of the rock quality value points 304b of FIG. 4 spans a porosity range of about 0.1 V/V to about 0.31 V/V, and spans a permeability range of about 7 md to about 101 md. The scaled distribution 500 of the rock quality value points 304b of FIG. 5 spans a porosity range of 0 to 1, and spans a permeability range of 0 to 1. As described, these scaled rock quality value points, including the respective values of porosity and permeability may be used in subsequent determinations.

In some embodiments, determining sampling subspaces (block 210) includes determining a number of subspaces ($n_s$) for each of the static rock types determined. Continuing with the prior example, determining sampling subspaces can include the CSS system 106 determining a number ($n_s$) of subspaces for each of the three static rock types determined.

In some embodiments, the sampling subspaces for static rock types are determined based on objective driven constraints. In a "minimum coverage" scenario (e.g., intended to provide a minimum number of samples for sampling the minimum, maximum and medium distributions within a static rock type), the distribution of each of the static rock types identified may be divided into three equal subspaces (e.g., $n_s$=3). The three equal subspaces may be defined by a first subspace, a second subspace and a third subspace defined, respectively, by a 0-33$^{rd}$ percentile, a 33$^{rd}$-66$^{th}$ percentile and a 66$^{th}$-100$^{th}$ percentile of the scaled rock quality values corresponding to the static rock type. In a "classification-constrained" scenario, the distribution of the static rock type may be divided into a given number of subspaces ($n_s$), equal to a number of different classes ($n_c$) identified in the static rock type. The number of classes may be defined, for example, based on a respective number of zonal, geological or facies-based classes (e.g., $n_s$=$n_c$). The "classification-constrained" scenario is intended to add integration flexibility to the proposed method to accommodate any pre-defined classification on the data. This pre-defined classification can be originated from geological or petrophysical sources. As an example of geological pre-defined classification, each static rock type can be classified using Wentworth Classification based on the range of its grain sizes as sand, mud, pebble or cobble etc. A static rock type may have two classes like Mud and Gravel (e.g., $n_s$=2), and in such a case, there are two subspaces in this static rock type from which sampling is done. As an example of petrophysical pre-defined classification, Stratigraphic Modified Lorenz plot, or Modified Lorenz plot, can be used to classify formations based on their flow capacity and storage capacity. In a certain rock type, there can be several classes that range from high flow/high storage capacity, high flow/low storage capacity to low flow/low storage capacity. In a "classification-constrained" scenario, additional petrophysical or geological methods that cluster/group the data can be incorporated into Winland or FZI approaches.

Continuing the above example, the first, the second and the third static rock types may be determined to correspond to three, four and five classes of zones, respectively, and the number of subspaces for the first, the second and the third static rock types ($n_{s1}$, $n_{s2}$, and $n_{s3}$) may be set to values of three, four and five, respectively. That is, in this example, the first, the second and the third static rock types may be divided into three, four and five subspaces, respectively. In an "optimal coverage" scenario (e.g., intended to optimize a coverage to cost ratio), the distribution of the static rock type may be divided into a given number of subspaces ($n_s$) based on heterogeneity within the static rock type, in an effort to increase sampling of heterogeneous static rock types or reduce sampling of homogeneous static rock types. In some embodiments, determining a given number of subspaces ($n_s$) for a static rock type includes determining the number of subspaces ($n_s$) for the static rock type to be equal to a number of subspaces ($S_i$) that maximizes the following objective function:

$$\sum_i^n VDP_{N_i} * S_i, \quad (2)$$

where, $$\sum_i^n S_i \le \frac{K}{k}, \quad (3)$$

-continued where $$M \leq S_i \leq \frac{K}{k} VDP_{N_i}, \quad (4)$$

where M is a minimum threshold, $S_i$ is an integer, $i \in \{1, 2, \ldots, n\}$ is an index for each of the respective static rock types determined, n is the number of static rock types determined (for the corresponding distribution of rock quality values), K is a total number of core samples to be selected from all of the static rock types determined (for the corresponding distribution of rock quality values), k is the number of core samples to select for each subspace of the static rock type, and $VDP_{N_i}$ is a normalized heterogeneity coefficient for the static rock type of index i. The minimum threshold (M) may be, for example, a value of 3, for a minimum coverage scenario honoring minimum, medium and max distributions. The normalized heterogeneity coefficient for a given static rock type may define a degree of heterogeneity of the core samples corresponding to the static rock type. In some embodiments, the normalized heterogeneity coefficient for a given static rock type is determined by way of normalization of a determined Dykstra-Parsons coefficient ($V_{dp}$) for the given static rock type. The Dykstra-Parsons coefficient ($V_{dp}$) for a given static rock type may provide a measure of dispersion of permeability values for the core samples corresponding to the static rock type. Details regarding application of the Dykstra-Parsons coefficient are described in Fitch P., Lovell M., Davies S., Pritchard T. and Harvey P., 2015, An integrated and quantitative approach to petrophysical heterogeneity, Marine and Petroleum Geology, Volume 63, 2015, Pages 82-96, ISSN 0264-8172, which is incorporated by reference. Continuing with the above example, a normalized heterogeneity coefficient may be determined for each of the three static rock types identified (e.g., $VDP_{N_1}$, $VDP_{N_2}$, and $VDP_{N_3}$), and the number of subspaces for the second static rock type (corresponding to the second region 308b and the cluster of rock quality value points 304b) may be determined to be three subspaces (e.g., $S_2=3$), based on application of the above objective function using the normalized heterogeneity coefficients, a total number of core samples to be selected from all of the static rock types being set to twenty (e.g., K=20), and the number of core samples to select for each subspace of the static rock type being set to three (e.g., k=3). A similar determination of the number of subspaces can be made for each of the other two static rock types. The total number of core samples to be selected from all of the static rock types (K) and the number of core samples to select for each subspace of the static rock type (k) may be selected by a well operator, or otherwise predefined.

In some embodiments, identifying selected core samples for the sampling subspaces (block 212) includes identifying, for each of the sampling subspaces identified, one or more core samples to be selected for an extensive core sample assessment. For example, identifying core samples for the sampling subspaces can include the CSS system 106 identifying, for each of the sampling subspaces identified, one or more of the core samples 102 to be selected for SCAL. In some embodiments, this includes for each subspace of each of the static rock types identified, identifying a given number of most similar scaled rock quality values in the subspace, the given number being equal to the number of core samples to select (k). Continuing with the above example, this can include, for each of the three subspaces of the second static rock type (corresponding to the second region 308b and the cluster of rock quality value points 304b) identifying the three most similar scaled rock quality values for each of the first, the second and the third subspaces, for a total of nine scaled rock quality values for the static rock type. In some embodiments, identifying a given number of most similar scaled rock quality values in a given subspace equal to the number of core samples to select (k) includes performing mathematical optimization, such as differential evolution optimization, or another suitable optimization process, for the subspace. This can include, for a given subspace: determining a sample percentile (Px) defining a percentile in the subspace to sample from; determining a percentile point ($\Phi_p$, $K_p$,) defined by a percentile porosity ($\Phi_p$) corresponding to the sample percentile (Px) and a percentile permeability ($K_p$) corresponding to the sample percentile (Px); and determining, from the scaled rock quality values in the subspace, the number (k) of closest scaled rock quality values in the subspace, defined by the number (k) of scaled rock quality values (e.g., ($\Phi_{c1},K_{c1}$), ... ($\Phi_{ck},K_{ck}$)) of the scaled rock quality values in the subspace, determined to be closest to the percentile point ($\Phi_p,K_p$). In some embodiments, the sample percentile ($Px_s$) for a subspace and the closest scaled rock quality values in the subspace are determined based on the following objective function for minimizing average Euclidean distance between points (or "compactness"):

$$\mu(\Gamma) = \frac{\sum_{u,w \in V(\Gamma)}^n d(u, w)}{\binom{k}{2}}, \quad (5)$$

subject to the constraints Px is integer, $Px_s - Px_{(s-1)} \leq$ percentile boundaries of the subspace (e.g., boundaries of $0\text{-}33^{rd}$ percentile for the first subspace of the example minimum coverage scenario described), where d(u,w) is the Euclidean distance between two points u and w, V(Γ) is the vertex set of k points corresponding to the most similar points to select given k=|V(Γ)| and S is number of subspaces in the corresponding static rock type (or cluster). Mathematical optimization may be conducted to find the most similar k points in the subspace of interest.

Figure 6A:
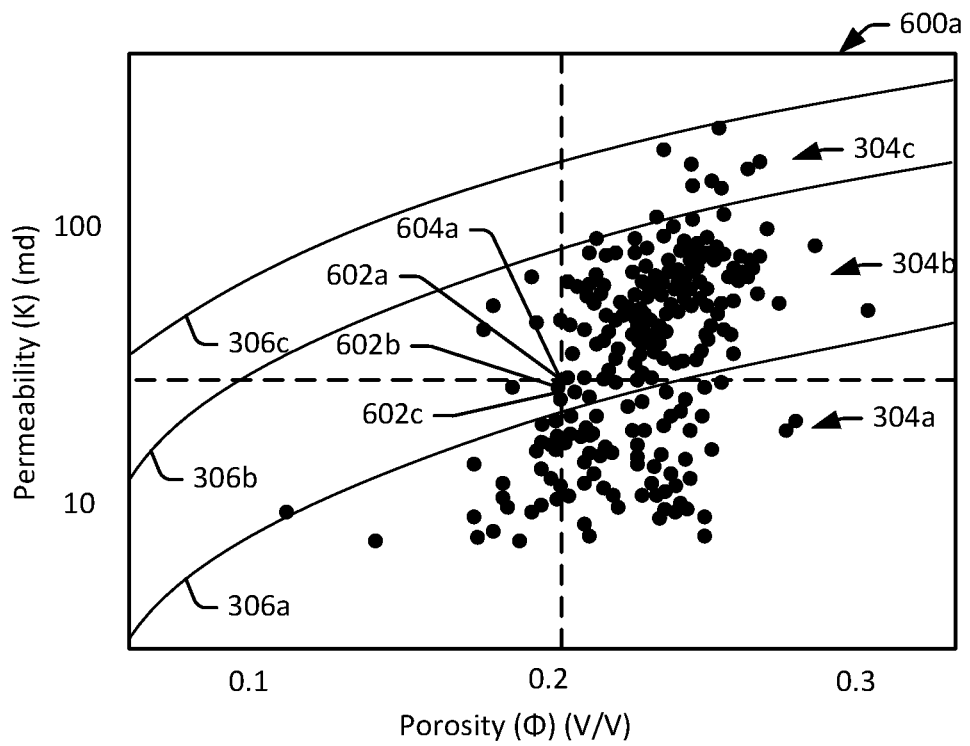
FIGS. 6A, 6B and 6C are charts that illustrate selected rock quality values from subspaces of a given static rock type in accordance with one or more embodiments.
Figure 6B:
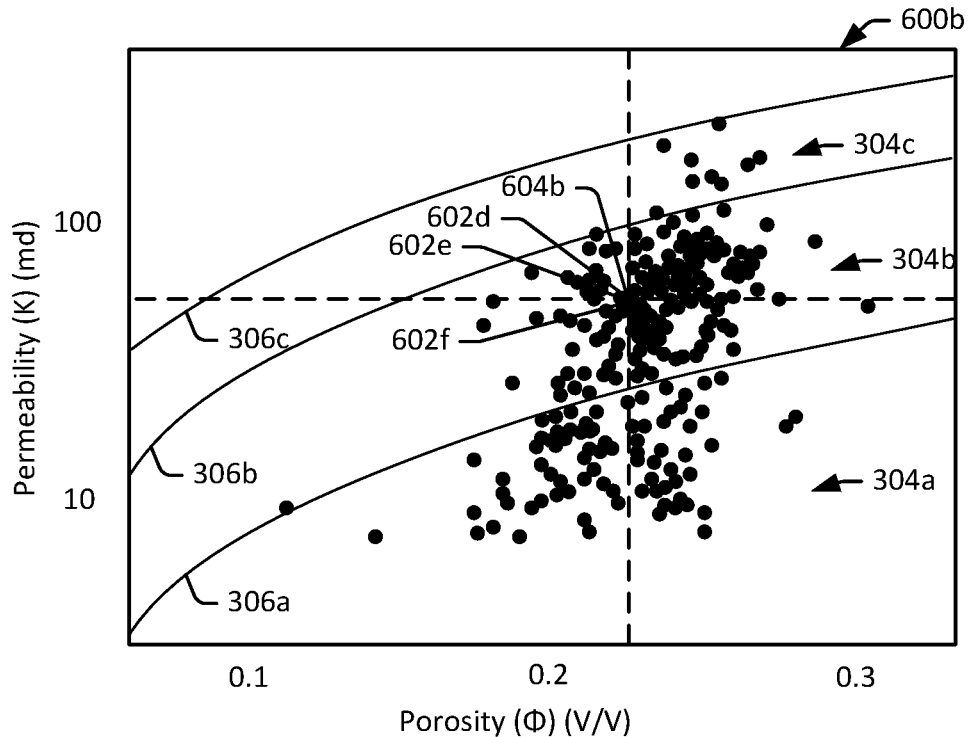
Figure 6C:
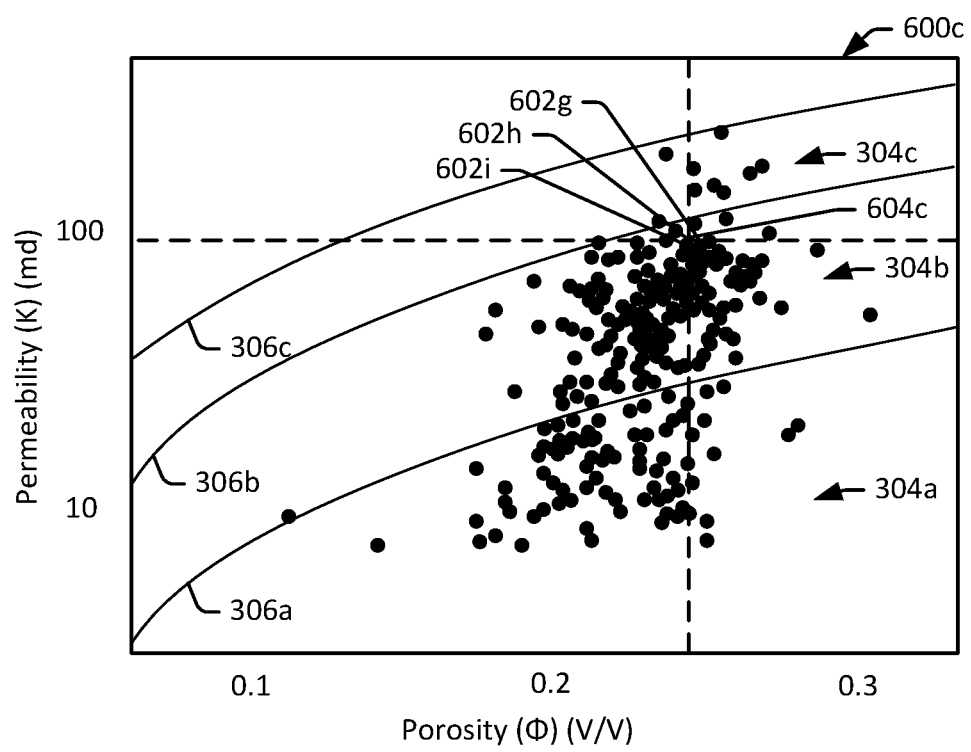

Continuing with the above example, a first sample percentile of 6% may be determined for the first subspace of the second static rock type (corresponding to the second region 308b and the cluster of rock quality value points 304b), as illustrated in chart 600a of FIG. 6A; a second sample percentile of 56% may be determined for the second subspace of the second static rock type, as illustrated in chart 600b of FIG. 6B, and a third sample percentile of 96% may be determined for the third subspace of the second static rock type, as illustrated in chart 600c of FIG. 6B. The percentile used is the statistical percentile. For two features, e.g., porosity and permeability, displayed as a cross-plot, the percentile is projected on both axes to identify percentile value (e.g., a value of 6% corresponds to 6% of the points falling below the percentile). Further, the three closest rock quality values 602a, 602b and 602c to a first percentile point 604a corresponding to the first sample percentile of 6% may be identified for the first subspace of the second static rock type; the three closest rock quality values 602d, 602e and 602f to a second percentile point 604b corresponding to the second sample percentile of 56% may be identified for the second subspace of the second static rock type; and the three closest rock quality values 602g, 602h and 602i to a third percentile point 604c corresponding to the third sample percentile of 96% may be identified for the third subspace of the second static rock type. For each of the rock quality values identified, the corresponding core sample 102 can be selected for an extensive core sample assessment. For example, a total of nine core samples 102, corresponding to rock quality values 602a-602i, can be selected for SCAL, and the nine core samples 102 can be added to the listing of selected core samples 112. A similar determination, and addition to the listing of selected core samples 112, can be made for each of the other two static rock types and their respective subspaces. The listing of selected core samples 112 may identify a subset of the set of core samples 102.

In some embodiments, method 200 includes analyzing the selected core samples (block 214). Analyzing the selected core samples can include subjecting one or more samples identified for an extensive core sample assessment, to an extensive analysis. Continuing with the above example, analyzing the selected core samples may include physically obtaining some or all of the core samples 102 identified in the listing of selected core samples 112, physically providing the core samples 102 to a test apparatus of the SCAL system 108, and the SCAL system 108 conducting a SCAL of the core samples 102 to generate corresponding SCAL data 114. The SCAL data 114 may include, for example, measurements of two-phase flow properties, relative permeability and capillary pressure for the core samples 102. The SCAL data 114 can provide an increased level of information regarding properties of the core samples 120 and the portions of the formation they were extracted from and, thus, can be useful in optimizing hydrocarbon production from wells. For example, log and seismic measurements for the formation can be calibrated based on the SCAL data 114. Further, well placements for a field of wells in the formation, well trajectories for wells in the formation, well completion designs for wells in the formation, well production strategies for wells in the formation, or other parameters for optimizing hydrocarbon production from wells in the formation, may be determined based on the SCAL data 114.

Figure 7A:
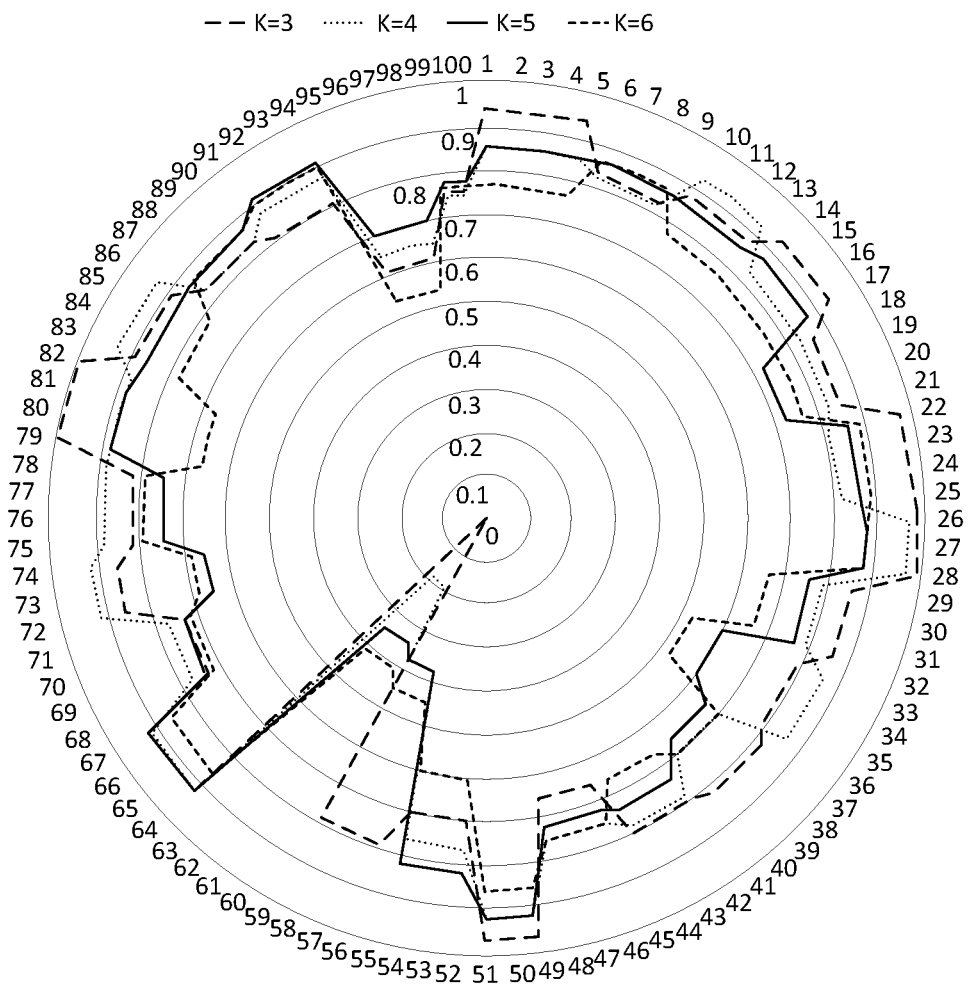
FIGS. 7A and 7B are diagrams that illustrate variations at different percentiles for a rock type in accordance with one or more embodiments.
Figure 7B:
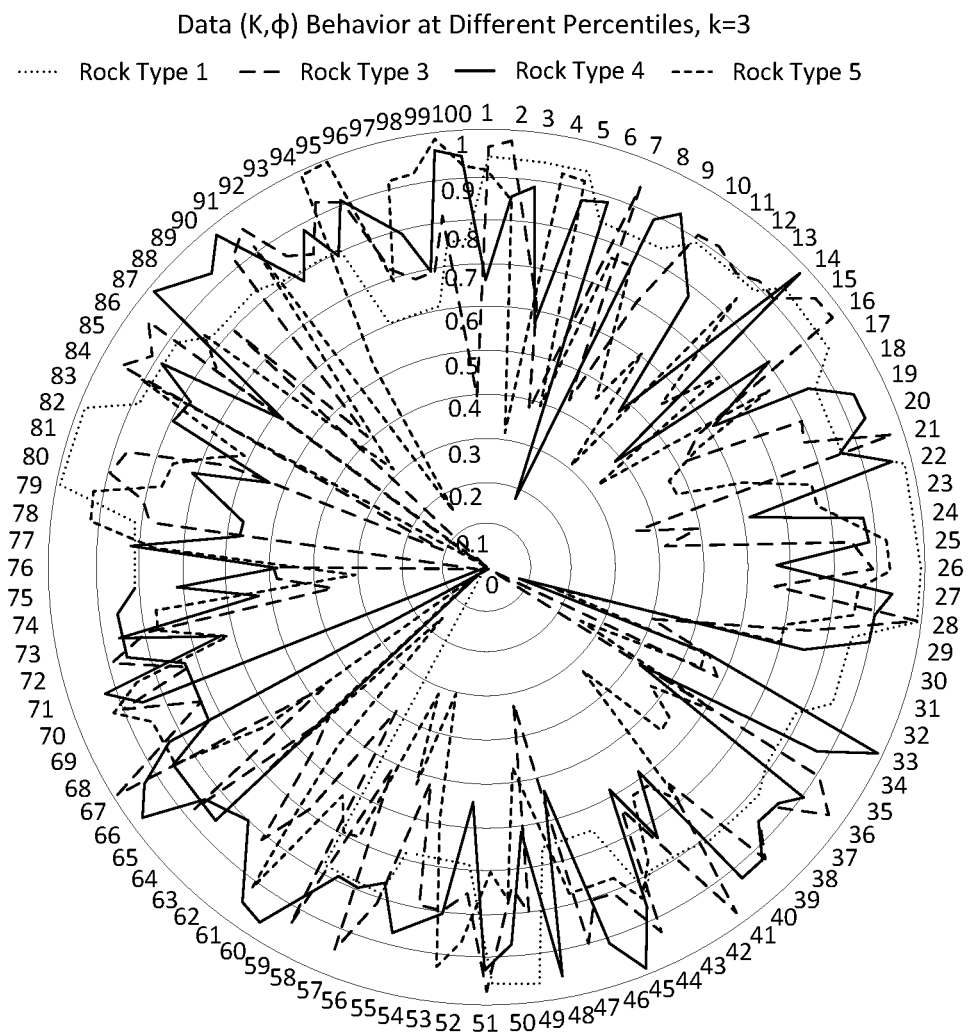

FIGS. 7A and 7B are diagrams that illustrate variations at different percentiles for rock types in accordance with one or more embodiments. FIG. 7A is a spider diagram that illustrates similarity of clock measures for different values of K (e.g., 3, 4, 5, and 6) for a given rock type. The diagram shows the percentile map for the one rock type, represented by the numbers surrounding the outermost circle, with the similarity scale being represented by nested circles ranging from 0 at the innermost circle to 1 at the outermost circle. The most similar samples change their location in the percentile map for the same rock type as the input parameter is changed, the number of most similar samples to be selected (k). This illustrates the sensitivity of selecting a total number of core samples (K) at different percentiles for a given rock type. FIG. 7B is a spider diagram that illustrates data (K, Φ) behavior at different percentiles for different rock types, with number of core samples (k) having a value of 3. The diagram shows different rock types having different data distributions and accordingly different percentile maps from which the most similar samples need to be selected using mathematical optimization.

Figure 8:
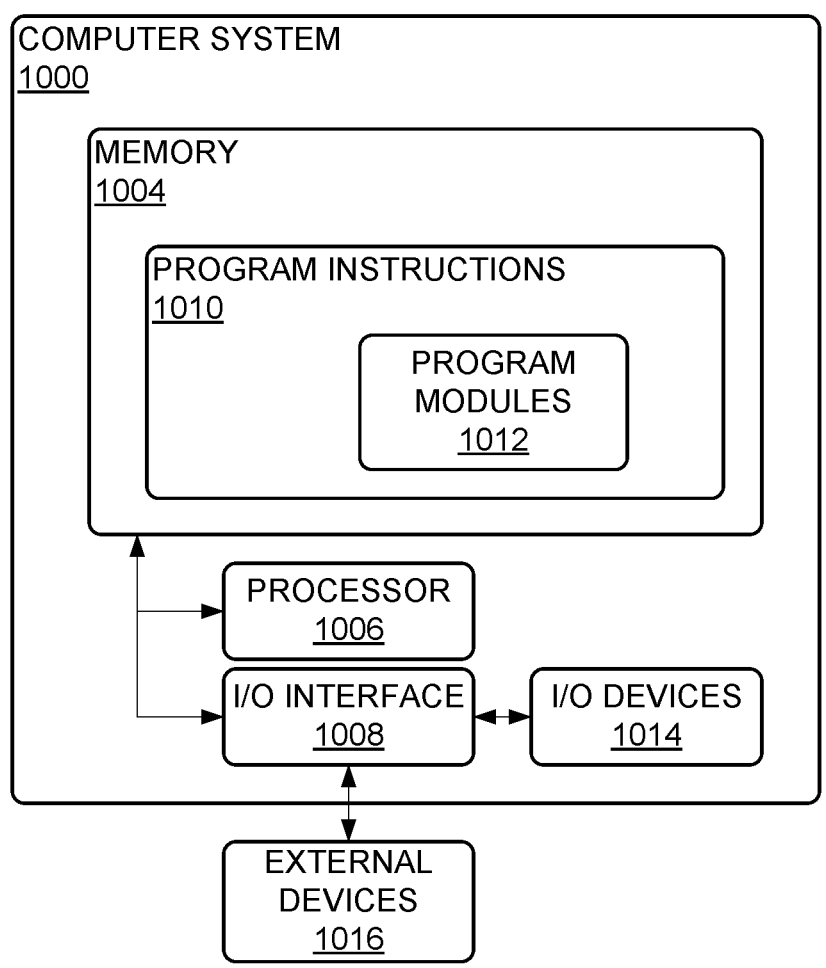
FIG. 8 is a diagram that illustrates an example computer system in accordance with one or more embodiments.

FIG. 8 is a diagram that illustrates an example computer system (or "system") 1000 in accordance with one or more embodiments. In some embodiments, the system 1000 is a programmable logic controller (PLC). The system 1000 may include a memory 1004, a processor 1006 and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), or bulk storage memory (for example, CD-ROM or DVD-ROM, hard drives). The memory 1004 may include a non-transitory computer-readable storage medium having program instructions 1010 stored thereon. The program instructions 1010 may include program modules 1012 that are executable by a computer processor (e.g., the processor 1006) to cause functional operations described, such as those described with regard to the core sample assessment system 103 or the method 200.

The processor 1006 may be any suitable processor capable of executing program instructions. The processor 1006 may include a central processing unit (CPU) that carries out program instructions (e.g., the program instructions of the program modules 1012) to perform the arithmetical, logical, or input/output operations described. The processor 1006 may include one or more processors. The I/O interface 1008 may provide an interface for communication with one or more I/O devices 1014, such as a joystick, a computer mouse, a keyboard, or a display screen (for example, an electronic display for displaying a graphical user interface (GUI)). The I/O devices 1014 may include one or more of the user input devices. The I/O devices 1014 may be connected to the I/O interface 1008 by way of a wired connection (e.g., an Industrial Ethernet connection) or a wireless connection (e.g., a Wi-Fi connection). The I/O interface 1008 may provide an interface for communication with one or more external devices 1016, such as a SCAL test apparatus, other computers and networks. In some embodiments, the I/O interface 1008 includes one or both of an antenna and a transceiver.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described are to be taken as examples of embodiments. Elements and materials may be substituted for those illustrated and described parts and processes may be reversed or omitted, and certain features of the embodiments may be utilized independently, all as would be apparent to one skilled in the art after having the benefit of this description of the embodiments. Changes may be made in the elements described without departing from the spirit and scope of the embodiments as described in the following claims. Headings are for organizational purposes only and are not meant to be used to limit the scope of the description.

It will be appreciated that the processes and methods described are example embodiments of processes and methods that may be employed in accordance with the techniques described. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method comprising:
obtaining core sample data for core samples extracted from a subsurface hydrocarbon formation, the core sample data comprising rock properties for each core sample of the core samples, the rock properties for each core sample comprising a porosity of the core sample, and a permeability of the core sample;
determining, for each core sample of the core samples and based on the core sample data, a rock quality value for the core sample, the rock quality value for the core sample defined by the porosity of the core sample and the permeability of the core sample;
determining, based on the rock quality values for the core samples, static rock types corresponding to the core samples, each of the static rock types corresponding to a subset of the core samples having a rock quality value corresponding to the static rock type;
for each of the static rock types identified:
scaling the rock quality values corresponding to the static rock type to generate scaled rock quality values corresponding to the static rock type, each scaled rock quality value comprising a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1;
determining, based on the scaled rock quality values, a number of subspaces ($n_s$) for the static rock type; and
for each subspace of the static rock type:
identifying, using mathematical optimization, a number (k) of most similar rock quality values in the subspace;
identifying a subset of the core samples corresponding to the most similar rock quality values identified for the subspace of the static rock type; and
conducting a special core analysis (SCAL) of each of the core samples of the subset of the core samples corresponding to the most similar rock quality values identified for the subspace of the static rock type, the SCAL comprising acquiring measurements of two-phase flow properties, relative permeability and capillary pressure for the core samples of the subset of the core samples corresponding to the most similar rock quality values identified for the subspace of the static rock type.

2. The method of claim 1, wherein determining the static rock types corresponding to the core samples comprises segmenting a distribution of the rock quality values using expectation-maximization mixture modeling clustering to determine the static rock types corresponding to the core samples.

3. The method of claim 2, wherein the expectation-maximization mixture modeling clustering comprises a flow zone indicator method or a Winland $R_{35}$ method.

4. The method of claim 2, wherein segmenting a distribution of the rock quality values using expectation-maximization mixture modeling clustering to determine the static rock types corresponding to the core samples comprises defining curves corresponding to expectation-maximization mixture modeling clustering, and determining a static rock type for each region bounded by at least one of the curves and containing at least one rock quality value of the distribution of the rock quality values.

5. The method of claim 1, wherein scaling the rock quality values corresponding to the static rock type to generate scaled rock quality values corresponding to the static rock type comprises:
determining a permeability range for the static rock type, the permeability range for the static rock type defined by a maximum permeability and a minimum permeability of the subset of the core samples corresponding to the static rock type;
determining a porosity range for the static rock type, the porosity range for the static rock type defined by a maximum porosity and a minimum porosity of the subset of the core samples corresponding to the static rock type;
scaling, based on the permeability range, the permeability (K) of each of the rock quality values corresponding to the static rock type according to the following relationship:

$$SK_i = \frac{K_i - \text{Min}(K)}{\text{Max}(K) - \text{Min}(K)},$$

where Max(K) is the maximum permeability of the subset of the core samples corresponding to the static rock type, and Min(K) is the minimum permeability of the subset of the core samples corresponding to the static rock type; and scaling, based on the porosity range, the porosity ($\Phi_i$) of each of the rock quality values corresponding to the static rock type according to the following relationship:

$$S\Phi_i = \frac{\Phi_i - \text{Min}(\Phi)}{\text{Max}(\Phi) - \text{Min}(\Phi)},$$

where Max($\Phi$) is the maximum porosity of the subset of the core samples corresponding to the static rock type, and Min($\Phi$) is the minimum porosity of the subset of the core samples corresponding to the static rock type.

6. The method of claim 1, wherein determining the number of subspaces ($n_s$) for the static rock type comprises employing a minimum coverage scenario comprising determining the number of subspaces ($n_s$) for the static rock type to be equal to three, and identifying three subspaces for the static rock type comprising a first subspace defined by a $0$-$33^{rd}$ percentile of the scaled rock quality values corresponding to the static rock type, a second subspace defined by a $33^{rd}$-$66^{th}$ percentile of the scaled rock quality values corresponding to the static rock type, and a third subspace defined by a $66^{th}$-$100^{th}$ percentile of the scaled rock quality values corresponding to the static rock type.

7. The method of claim 1, wherein determining a number of subspaces ($n_s$) for the static rock type comprises employing a classification constrained scenario comprising determining a number of different classes identified in the static rock type ($n_c$), and determining the number of subspaces ($n_s$) for the static rock type to be equal to the number of different classes identified in the static rock type ($n_c$).

8. The method of claim 1, wherein determining a number of subspaces ($n_s$) for the static rock type comprises employing an optimal coverage scenario comprising:
   determining a heterogeneity coefficient for the static rock type, the heterogeneity coefficient for the static rock type defining a degree of heterogeneity of the subset of the core samples corresponding to the static rock type; and
   determining the number of subspaces ($n_s$) for the static rock type based on heterogeneity within the static rock type.

9. The method of claim 8, wherein determining the number of subspaces ($n_s$) for the static rock type based on heterogeneity within the static rock type comprises determining the number of subspaces ($n_s$) for the static rock type to be equal to a number of subspaces ($S_i$) that maximizes the following objective function:

$$\sum_i^n VDP_{N_i} * S_i,$$

where, $$\sum_i^n S_i \le \frac{K}{k},$$

where $$M \le S_i \le \frac{K}{k} VDP_{N_i},$$

where M is a minimum threshold, $S_i$ is an integer, $i \in \{1,2, n\}$ is an index for each of the respective static rock types determined, n is a number of static rock types determined, K is a total number of core samples to be selected from the static rock types determined, k is the number of core samples to select for each subspace of the static rock type, and $VDP_{N_i}$ is a normalized heterogeneity coefficient for the static rock type of index i.

10. The method of claim 8, wherein the heterogeneity coefficient for the static rock type comprises a normalized Dykstra-Parsons coefficient ($V_{dp}$) determined for the static rock type.

11. The method of claim 1, wherein identifying the number of most similar scaled rock quality values in the subspace comprises:
   determining a sample percentile (Px) defining a percentile in the subspace to sample from;
   determining a percentile point $\Phi_p$, $K_p$,) defined by a percentile porosity ($\Phi_p$) corresponding to the sample percentile (Px) and a percentile permeability ($K_p$) corresponding to the sample percentile (Px); and
   determining, from the rock quality values in the subspace, a number of closest scaled rock quality values in the subspace that is defined by a number of rock quality values of the rock quality values in the subspace determined to be closest to the percentile point ($\Phi_p$ $K_p$,).

12. The method of claim 1, wherein identifying the subset of the core samples corresponding to the most similar rock quality values identified for the subspace of the static rock type comprises generating a listing of selected core samples comprising the subset of the core samples corresponding to the most similar rock quality values identified for the subspace of the static rock type.

13. The method of claim 1, wherein conducting a SCAL of each of the core samples of the subset of the core samples corresponding to the most similar rock quality values identified for the subspace of the static rock type comprises generating SCAL core analysis data, and the method further comprising, based on the SCAL core analysis data:
   calibrating log or seismic measurements; or
   determining well placements, well trajectories, well completion designs, or well production strategies for optimizing hydrocarbon production from wells.

14. The method of claim 1, further comprising conducting coring operations to extract the core samples from the subsurface hydrocarbon formation.

15. A non-transitory computer readable storage medium comprising program instructions stored thereon that are executable by a processor to perform the following operations:
   obtaining core sample data for core samples extracted from a subsurface hydrocarbon formation, the core sample data comprising rock properties for each core sample of the core samples, the rock properties for each core sample comprising a porosity of the core sample, and a permeability of the core sample;
   determining, for each core sample of the core samples and based on the core sample data, a rock quality value for the core sample, the rock quality value for the core sample defined by the porosity of the core sample and the permeability of the core sample;
   determining, based on the rock quality values for the core samples, static rock types corresponding to the core samples, each of the static rock types corresponding to a subset of the core samples having a rock quality value corresponding to the static rock type;
   for each of the static rock types identified:
      scaling the rock quality values corresponding to the static rock type to generate scaled rock quality values corresponding to the static rock type, each scaled rock quality value comprising a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1;

determining, based on the scaled rock quality values, a number of subspaces ($n_s$) for the static rock type; and for each subspace of the static rock type:

identifying, using mathematical optimization, a number (k) of most similar rock quality values in the subspace;

identifying a subset of the core samples corresponding to the most similar rock quality values identified for the subspace of the static rock type; and conducting a special core analysis (SCAL) of each of the core samples of the subset of the core samples corresponding to the most similar rock quality values identified for the subspace of the static rock type, the SCAL comprising acquiring measurements of two-phase flow properties, relative permeability and capillary pressure for the core samples of the subset of the core samples corresponding to the most similar rock quality values identified for the subspace of the static rock type.

16. A system comprising:

a special core analysis (SCAL) system; and a core samples selection system configured to perform the following operations:

obtaining core sample data for core samples extracted from a subsurface hydrocarbon formation, the core sample data comprising rock properties for each core sample of the core samples, the rock properties for each core sample comprising a porosity of the core sample, and a permeability of the core sample;

determining, for each core sample of the core samples and based on the core sample data, a rock quality value for the core sample, the rock quality value for the core sample defined by the porosity of the core sample and the permeability of the core sample;

determining, based on the rock quality values for the core samples, static rock types corresponding to the core samples, each of the static rock types corresponding to a subset of the core samples having a rock quality value corresponding to the static rock type; and for each of the static rock types identified:

scaling the rock quality values corresponding to the static rock type to generate scaled rock quality values corresponding to the static rock type, each scaled rock quality value comprising a corresponding scaled permeability value and a corresponding scaled porosity value, such that the scaled porosity values of the scaled rock quality values corresponding to the static rock type are scaled to span a range of 0 to 1 and the scaled permeability values of the scaled rock quality values corresponding to the static rock type are scaled to span a range of 0 to 1;

determining, based on the scaled rock quality values, a number of subspaces ($n_s$) for the static rock type;

for each subspace of the static rock type:

identifying, using mathematical optimization, a number (k) of most similar rock quality values in the subspace; and identifying a subset of the core samples corresponding to the most similar rock quality values identified for the subspace of the static rock type, wherein the SCAL system is configured to conduct a special core analysis (SCAL) of each of the core samples of the subset of the core samples corresponding to the most similar scaled rock quality values identified for the subspace of the static rock type, the SCAL comprising acquiring measurements of two-phase flow properties, relative permeability and capillary pressure for the core samples of the subset of the core samples corresponding to the most similar rock quality values identified for the subspace of the static rock type.

* * * * *